United States Patent [19]

Marsan et al.

[11] Patent Number: 5,019,063
[45] Date of Patent: May 28, 1991

[54] ABSORBENT ARTICLES CONTAINING MECHANICAL PULP AND POLYMERIC GELLING MATERIAL

[75] Inventors: Mario S. Marsan, Cincinnati; Leonard R. Thompson, Fairfield, both of Ohio

[73] Assignee: The Procter & Gamble Company, Cincinnati, Ohio

[21] Appl. No.: 428,524

[22] Filed: Oct. 30, 1989

[51] Int. Cl.⁵ .............................................. A61F 13/15
[52] U.S. Cl. ................... 604/368; 604/370; 604/372; 604/375; 604/376; 604/378; 604/385.1
[58] Field of Search ............... 604/368, 370, 372, 375, 604/376, 378, 385.1

[56] References Cited

U.S. PATENT DOCUMENTS

| | | | |
|---|---|---|---|
| 3,587,579 | 10/1968 | Sabee | 128/287 |
| 3,597,299 | 8/1971 | Thomas et al. | 161/57 |
| 3,683,916 | 8/1972 | Mesek et al. | 128/287 |
| 3,683,921 | 8/1972 | Brooks et al. | 128/296 |
| 3,732,867 | 5/1973 | Money | 128/290 R |
| 3,768,479 | 10/1973 | Widlund | 128/287 |
| 3,867,940 | 2/1975 | Mesek et al. | 128/287 |
| 3,927,673 | 12/1975 | Taylor | 128/287 |
| 4,141,772 | 2/1979 | Buell | 156/227 |
| 4,235,237 | 11/1980 | Mesek et al. | 128/284 |
| 4,327,729 | 5/1982 | King | 128/287 |
| 4,392,862 | 7/1983 | Marsan et al. | 604/366 |
| 4,673,402 | 6/1987 | Weisman et al. | 604/368 |
| 4,765,780 | 8/1988 | Angstadt | 406/123 |
| 4,806,408 | 2/1989 | Pierre et al. | 428/76 |
| 4,888,231 | 12/1989 | Angstadt | 604/368 |
| 4,904,440 | 2/1990 | Angstadt | |

FOREIGN PATENT DOCUMENTS 1522569  6/1976  United Kingdom .

Primary Examiner—Randall L. Green
Assistant Examiner—K. M. Reichle
Attorney, Agent, or Firm—Leonard W. Lewis

[57] ABSTRACT

A disposable, absorbent diaper comprising a topsheet, a liquid impervious backsheet associated with the topsheet, and an absorbent core disposed between the topsheet and the backsheet, wherein the absorbent core has a dusting layer of mechanical pulp fibers, a continuous primary layer of mechanical pulp fibers containing from about 8% to about 60%, on a total primary layer dry weight basis, of discrete particles of polymeric gelling material, and a water-permeable core reinforcing layer disposed between the dusting layer and the primary layer. The mechanical pulp fibers, preferably chemi-thermomechanical pulp fibers, have an average fiber length of at least about 1.9 mm and are in a highly disintegrated condition.

12 Claims, 3 Drawing Sheets

2

ABSORBENT ARTICLES CONTAINING MECHANICAL PULP AND POLYMERIC GELLING MATERIAL

FIELD OF THE INVENTION

This invention relates to absorbent, disposable articles having an absorbent core comprising mechanical pulp fibers and discrete particles of a polymeric gelling material. More particularly, this invention relates to absorbent, disposable diapers having an absorbent core of mechanical pulp fibers and polymeric gelling material, wherein the core is internally reinforced with a core reinforcing element.

BACKGROUND OF THE INVENTION

Absorbent articles, such as disposable diapers, are generally provided with absorbent cores to receive and retain body fluids. In order for such absorbent articles to function efficiently, the absorbent cores must quickly acquire body liquids into the structure from the point of application and subsequently distribute the body liquids within and throughout the absorbent core to provide maximum absorbency and containment. In order to efficiently perform these functions, the absorbent core should substantially maintain its shape during manufacture, shipping and packing, and fitting and usage by the user, including usage subsequent to initial wetting by the user.

Various material have been employed as the absorbent media in disposable absorbent articles. The most commonly utilized absorbent media in recent years is chemically pulped wood fibers provided in a highly individualized, i.e., disintegrated, state referred to in the art as "fluff". Fluff is typically air-laid in the form of webs, which are then utilized as the absorbent core of absorbent disposable articles.

Performance of disposable diapers has, in recent years, been improved through the incorporation into the absorbent cores of polymeric gelling materials, which have the capability of absorbing fluids to form gels which lock-away the fluids and which do not release such fluids upon application of pressure to the absorbent core (e.g., by the user rolling about after discharging fluids into the absorbent article). Due, at least in part, to the performance capabilities of disposable absorbent articles having absorbent cores of chemical pulp fibers and polymeric gelling materials, the trend has been to manufacture disposable articles having absorbent cores which are thinner, and of higher density, than conventionally practiced prior to the widespread usage of polymeric gelling materials.

Although the chemically pulped fibers commonly used in disposable absorbent articles provide good overall performance, especially in terms of web integrity, it is desirable to utilize fibers in disposable absorbent articles which are more efficient from the standpoint of utilization of natural resources. Typically, the chemically pulped fibers that are utilized as fluff in absorbent articles constitute only about 40% of the wood source from which the fibers are processed. Additionally, it is desirable to provide absorbent cores of fibers made by processes which require reduced levels of pulping chemicals (e.g., sulfate in the "Kraft" chemical pulping process) relative to processes conventionally used to make chemical pulp fibers. One type of absorbent fibrous media which fits these objectives is known generally as mechanical pulp, which term includes such variants as thermomechanical pulp and chemithermomechanical pulp. The processes used to make these mechanical pulps, which are known to those skilled in the art, provide substantially higher yields (typically in excess of 85%) than chemical pulp processes. In addition, mechanical pulp processes involve reduced usage of processing chemicals.

In spite of the above advantages, mechanically pulped fibers have not been commonly utilized in commercially marketed disposable absorbent articles, except in countries where environmental concerns are especially prevalent. One of the drawbacks conventionally associated with mechanically pulped fibers is that they provide relatively low strength when formed into air-laid webs. The use of such low strength webs as absorbent cores in disposable absorbent articles has conventionally required the use of a strength-imparting envelope. Webs of low strength mechanical fibers including an interior reinforcing layer in addition to the required tissue envelope layers are also known. See, for example, U.S. Pat. No. 4,327,729, L. W. King, issued May 4, 1982. Unfortunately, the presence of an additional structural element between the absorbent core and the topsheet of an absorbent article can impede the rapid absorption of fluids discharged during use. Other drawbacks traditionally associated with low strength mechanical pulp webs are that mechanical pulp fibers are less hydrophilic than chemical pulp fibers and have reduced ability to retain fluids in the void spaces between fibers. Both of these factors contribute to reduced performance in the context of absorbent article performance relative to chemical pulp fibers.

In view of these drawbacks, it is desirable to provide a disposable absorbent diaper which incorporates, as its primary absorbent fibrous media, high yield, mechanical pulp fibers. It is an object of the invention to provide such a disposable absorbent article which has absorbency and containment performance, as well as absorbent core structural integrity, comparable to disposable absorbent diapers having chemically pulped fibers as the principal absorbent fibrous media. It is particularly an object of this invention to provide disposable absorbent diapers having thin absorbent cores made from mechanical pulp fibers which provide absorbency and containment performance, as well as absorbent core structural integrity, comparable to disposable absorbent articles chemical pulp fibers and polymeric gelling materials incorporated therein.

These objectives, and other benefits as may become apparent to those skilled in the art, are believed to be achieved by the invention which is described hereinafter.

SUMMARY OF THE INVENTION

It has been found that the above objects can be met by disposable absorbent diapers comprising
(a) a topsheet;
(b) a liquid impervious backsheet associated with said topsheet; and
(c) an absorbent core disposed between said topsheet and said backsheet, said absorbent core having:
  (i) a dusting layer of mechanical pulp fibers;
  (ii) a continuous primary layer of mechanical pulp fibers containing from about 8% to about 60%, on a total primary layer dry weight basis, of discrete particles of polymeric gelling material; and (iii) a water-permeable core reinforcing layer disposed between said dusting layer and said primary layer;
wherein the mechanical pulp fibers have an average fiber length of at least about 1.9 mm and are characterized by a Disintegration State of at least about 85%. The dusting layer has an average basis weight of between about 0.01 g/cm² and about 0.20 g/cm² and a density of between about 0.06 g/cm³ and about 0.30 g/cm³. The primary layer has a basis weight of between about 0.01 g/cm² and about 0.20 g/cm² and a density between about 0.06 g/cm³ and about 0.30 g/cm³. Also, the fibrous web is oriented such that said primary layer is disposed toward the topsheet and the dusting layer is disposed toward the backsheet. The preferred mechanical pulp fibers are chemically treated or modified thermomechanical pulp fibers. In an especially preferred embodiment, the diaper is characterized by the absence of any structural elements interposed between the topsheet and the primary layer and between said backsheet and the dusting layer. Additionally, in the preferred embodiments, the Disintegration State of the fibers is at least about 90%, more preferably at least about 95%.

While the specification concludes with claims which particularly point out and distinctly claim the subject matter regarded as constituting the present invention, it is believed that the invention will be better understood from the following description taken in conjunction with the accompanying drawings.

DETAILED DESCRIPTION OF THE INVENTION

The present invention is described below in detail in the context of providing airlaid fibrous webs for use as absorbent cores in disposable absorbent diapers.

Figure 1:
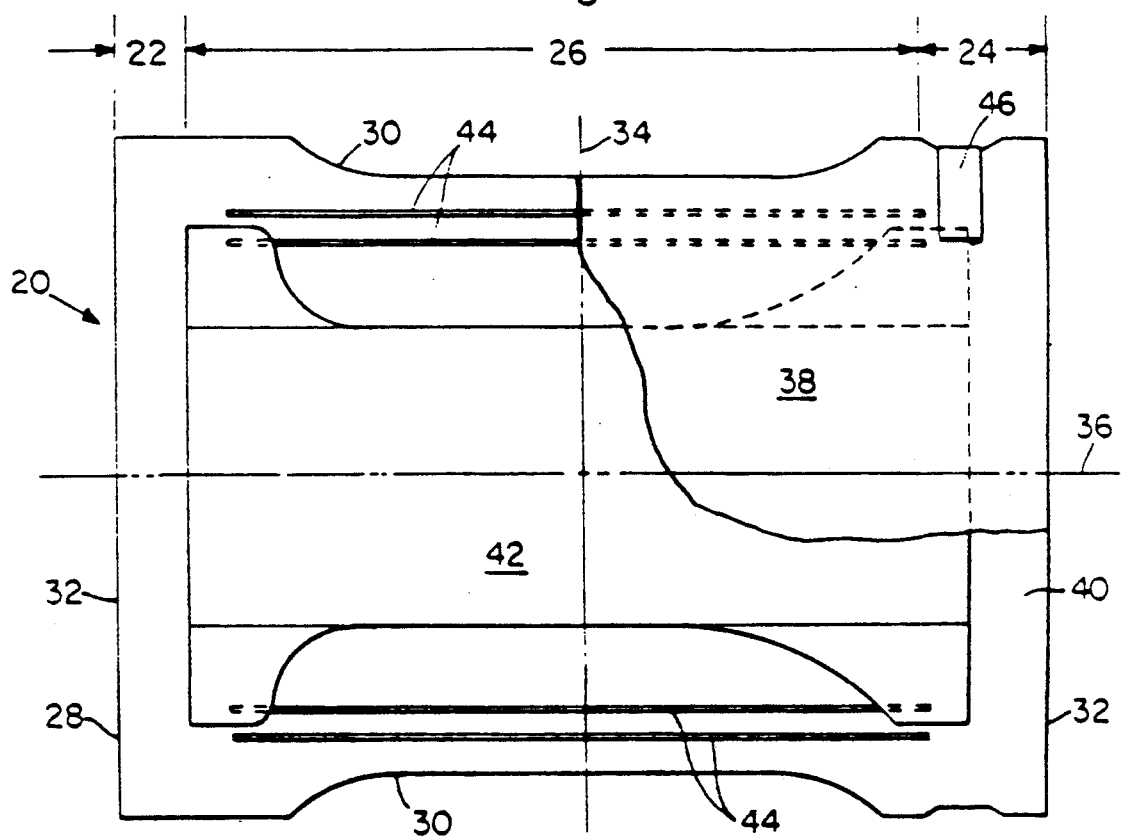
FIG. 1 is a plan view of a disposable diaper embodiment of the present invention wherein most of the topsheet has been cut-away to more clearly show the underlying absorbent core of the diaper.

A preferred embodiment of a disposable absorbent diaper is shown, as diaper 20, in FIG. 1. As used herein, the term "diaper" refers to a garment generally worn by infants and incontinent persons (including adults) that is worn about the lower torso of the wearer. It should be understood, however, that the present invention is also applicable to other disposable absorbent articles corresponding in structure to the diapers described herein.

FIG. 1 is a plan view of the diaper 20 of the present invention in its flat-out, uncontracted state (i.e., with all elastic induced contraction removed) with portions of the structure being cut-away to more clearly show the construction of the diaper 20 and with the portion of the diaper 20 which contacts the wearer facing the viewer.

The diaper 20 is shown in FIG. 1 to have a front waistband region 22, a back waistband region 24, a crotch region 26 and a periphery 28 which is defined by the outer edges of the diaper in which the longitudinal edges are designated 30 and the end edges are designated 32. The diaper additionally has a transverse centerline which is designated 34 and a longitudinal centerline which is designated 36.

The diaper 20 comprises a liquid pervious topsheet 38; a liquid impervious backsheet 40; an absorbent member 42; and elastic members 44. While the topsheet 38 the backsheet 40, the absorbent core 42, and the elastic members 44 may be assembled in a variety of well known configurations, a preferred diaper configuration is described generally in U.S. Pat. No. 3,860,003 entitled "Contractable Side Portions for Disposable Diaper", which issued to K. B. Buell on Jan. 14, 1975, and which patent is incorporated herein by reference.

FIG. 1 shows a preferred embodiment of the diaper 20 in which the topsheet 38 and the backsheet 40 are co-extensive and have length and width dimensions generally larger than those of the absorbent core 42. The topsheet 38 is associated with and superimposed on the backsheet 40 thereby forming the periphery 28 of the diaper 20. The periphery 28 defines the outer perimeter or the edges of the diaper 20. The periphery 28 comprises the end edges 32 and longitudinal edges 30.

The diaper 20 has front and back waistband regions 22 and 24 respectively extending, from the end edges 32 of the diaper periphery 28 toward the transverse centerline 34 of the diaper a distance from about 2% to about 10%, preferably about 5%, of the length of the diaper 20. The waistband regions comprise those upper portions of the diaper 20, which when worn, encircle the waist of the wearer. The crotch region 26 is that portion of the diaper 20 between the waistband regions 22 and 24, and comprises that portion of the diaper 20 which, when worn, is positioned between the legs of the wearer and covers the lower torso of the wearer. Thus, the crotch region 26 defines the area of typical liquid deposition for a diaper 20 or other disposable absorbent article.

The topsheet 38 is compliant, soft feeling, and non-irritating to the wearer's skin. Further, the topsheet 38 is liquid pervious permitting liquids to readily penetrate through its thickness. A suitable topsheet 38 may be manufactured from a wide range of materials, such as porous foams, reticulated foams, apertured plastic films, natural fibers (e.g., wood or cotton fibers), synthetic fibers (e.g., polyester or polypropylene fibers) or from a combination of natural and synthetic fibers. Preferably, the topsheet 38 is made of a hydrophobic material to isolate the wearer's skin from liquids in the absorbent core 42. The topsheet can be treated with a surfactant in order to facilitate penetration of fluid through said topsheet, however the topsheet should remain hydrophobic relative to the fibrous web, shown as absorbent core 42 in FIG. 1.

A preferred topsheet 38 comprises staple length polypropylene fibers having a denier of about 1.5, such as Hercules type 151 polypropylene marketed by Hercules, Inc. of Wilmington, Del. As used herein, the term "staple length fibers" refers to those fibers having a length of at least about 15.9 mm (0.62 inches).

There are a number of manufacturing techniques which may be used to manufacture the topsheet 38. For example, the topsheet 38 may be woven, non-woven, spunbonded, carded, or the like. A preferred topsheet is carded, and thermally bonded by means well known to those skilled in the fabrics art. Preferably, the topsheet 38 has a weight from about 18 to about 25 grams per square meter, a minimum dry tensile strength of at least about 400 grams per centimeter in the machine direction and a wet tensile strength of at least about 55 grams per centimeter in the cross machine direction.

The backsheet 40 is impervious to liquids and is preferably manufactured from a thin plastic film, although other flexible liquid impervious materials may be used. The backsheet 40 prevents the exudates absorbed and contained in the absorbent core 42 from wetting articles which contact the diaper 20 such as bed sheets and undergarments. Preferably, the backsheet 40 is polyethylene film having a thickness of from about 0.012 mm (0.5 mil) to about 0.051 centimeters (2.0 mils), although other flexible, liquid impervious materials may be used. As used herein, the term "flexible" refers to materials which are compliant and which will readily conform to the general shape and contours of the wearer's body.

A suitable polyethylene film is manufactured by Monsanto Chemical Corporation and marketed in the trade as Film No. 8020. The backsheet 40 is preferably embossed and/or matte finished to provide a more clothlike appearance. Further, the backsheet 40 may permit vapors to escape from the absorbent core 42 while still preventing exudates from passing through the backsheet 40.

The size of the backsheet 40 is dictated by the size of the absorbent core 42 and the exact diaper design selected. In a preferred embodiment, the backsheet 40 has a modified hourglass-shape extending beyond the absorbent core 42 a minimum distance of at least about 1.3 centimeters to about 2.5 centimeters (about 0.5 to about 1.0 inch) around the entire diaper periphery 28.

The topsheet 38 and the backsheet 40 are associated together in any suitable manner. As used herein, the term "associated" encompasses configurations whereby the topsheet 38 is directly joined to the backsheet 40 by affixing the topsheet 38 directly to the backsheet 40, and configurations whereby the topsheet 38 is indirectly joined to the backsheet 40 by affixing the topsheet 38 to intermediate members which in turn are affixed to the backsheet 40. In a preferred embodiment, the topsheet 38 and the backsheet 40 are affixed directly to each other in the diaper periphery 28 by attachment means (not shown) such as an adhesive or any other attachment means as known in the art. For example, a uniform continuous layer of adhesive, a patterned layer of adhesive, or an array of separate lines or spots of adhesive may be used to affix the topsheet 38 to the backsheet 40.

Tape tab fasteners 46 are typically applied to the back waistband region 24 of the diaper 20 to provide a fastening means for holding the diaper on the wearer. Only one of the tape tab fasteners is shown in FIG. 1. The tape tab fasteners 46 can be any of those well known in the art, such as the fastening tape disclosed in U.S. Pat. No. 3,848,594, issued to K. B. Buell on Nov. 19, 1974, which patent is incorporated herein by reference. These tape tab fasteners 46 or other diaper fastening means, such as pins, are typically applied near the corners of the diaper 20.

The elastic members 44 are disposed adjacent the periphery 28 of the diaper 20, preferably along each longitudinal edge 30 so that the elastic members 44 tend to draw and hold the diaper 20 against the legs of the wearer. Alternatively, the elastic members 44 may be disposed adjacent either or both of the end edges 32 of the diaper 20 to provide a waistband as well as or rather than leg cuffs. For example, a suitable waistband is disclosed in U.S. Pat. No. 4,515,595 issued to David J. Kievit and Thomas F. Osterhage on May 7, 1985, which patent is herein incorporated by reference. In addition, a method and apparatus suitable for manufacturing a disposable diaper having elastically contractible elastic members is described in U.S. Pat. No. 4,081,301 entitled "Method and Apparatus for Continuously Attaching Discrete, Stretched Elastic Strands to Predetermined Isolated Portions of Disposable Absorbent Products" which issued to K. B. Buell on Mar. 28, 1978 and which patent is incorporated herein by reference.

The elastic members 44 are secured to the diaper 20 in an elastically contractible condition so that in a normally unrestrained configuration, the elastic members 44 effectively contract or gather the diaper 20. The elastic members 44 can be secured in an elastically contractible condition in at least two ways. For example, the elastic members 44 may be stretched and secured while the diaper 20 is in an uncontracted condition. Alternatively, the diaper 20 may be contracted, for example, by pleating, and the elastic members 44 secured and connected to the diaper 20 while the elastic members 44 are in their unrelaxed or unstretched condition.

In the embodiment illustrated in FIG. 1, the elastic members 44 extend essentially the entire length of the diaper 20 in the crotch region 26. Alternatively the elastic members 44 may extend the entire length of the diaper 20, or any other length suitable to provide elastically contractable line. The length of the elastic members 44 is dictated by the diapers' design The elastic members 44 may take a multitude of configurations. For example, the width of the elastic members 44 may be varied from about 25 millimeters (0.01 inches) to about 25 millimeters (1.0 inch) or more; the elastic members 44 may comprise a single strand of elastic material or may comprise several parallel or non-parallel strands of elastic material; or the elastic members 44 may be affixed to the diaper in any of several ways which are known in the art. For example, the elastic members 44 may be ultrasonically bonded, heat and pressure sealed into the diaper 20 using a variety of bonding patterns or the elastic members 44 may simply be glued to the diaper 20.

The absorbent core 42 is an air-laid fibrous web positioned between the topsheet 38 and the backsheet 40 to form the diaper 20. The absorbent core 42 is generally compressible, conformable, non-irritating to the wearer's skin, and capable of absorbing and retaining liquids and certain body exudates.

Figure 2:
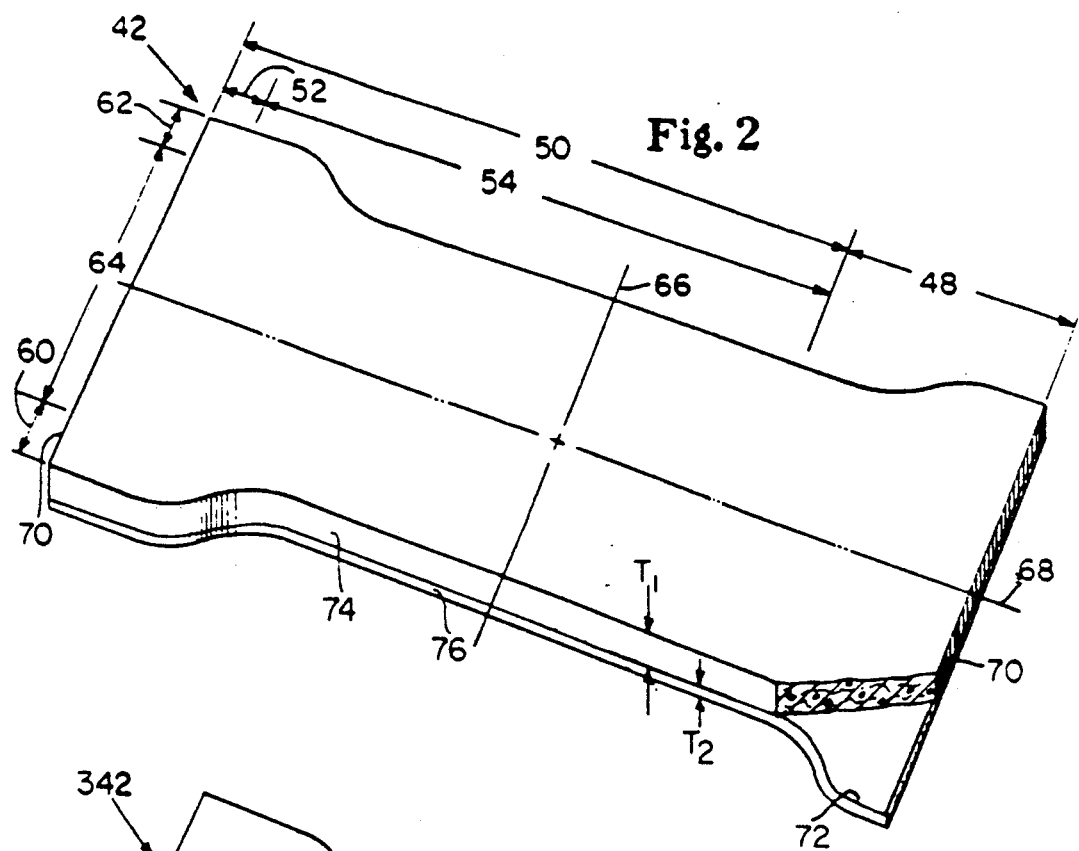
FIG. 2 is a perspective view of the absorbent core of the disposable diaper of FIG. 1.

FIG. 2 is a perspective view of a preferred embodiment of the absorbent core 42 of the present invention. The absorbent core 42 is shown in FIG. 2 to comprise a back section 48 and a front section 50 The front section 50 is shown to have an end region 52 and a deposition region 54 Further, the front section 50 is transversely divided into three regions comprising two transversely spaced ear regions 60 and 62 respectively, and a central region 64. The absorbent core 42 additionally has a transverse centerline which is designated 66 and a longitudinal centerline which is designated 68.

The absorbent core 42 has a back section 48 and a front section 50 that is contiguous with the back section 48. The back section 48 and the front section 50 of the absorbent core 42 extend respectively from the end edges 70 of the absorbent core 42 toward the transverse centerline 66, the front portion 50 extending a distance from about one half to about three-fourths, preferably about two-thirds, of the length of the absorbent core 42. The front section 50 is preferably greater than one half of the total length of the absorbent core 42 so that it will encompass all of the area of typical liquid deposition of an absorbent core 42 when it is placed in a diaper or other absorbent article.

The front portion 50 has an end region 52 and a deposition region 54. The end region 52 comprises that portion of the front section 50 extending from the respective end edge 70 of the absorbent member 42 toward the transverse centerline 66 a distance from about 2% to about 10%, preferably about 5%, of the length of the absorbent core 42. The deposition region 54 comprises that portion of the front portion 50 that is contiguous with and positioned between the end region 52 and the back section 48 and encompasses the area of typical liquid deposition of the absorbent core 42.

The front portion 50 further has two transversely spaced ear regions 60 and 62 respectively, and a central region 64 disposed intermediate said ear regions 60 and 62. The ear regions 60 and 62 comprise those portions which generally extend from the longitudinal edges 30 of the periphery 28 toward the longitudinal centerline a distance from about one-tenth to about one-third of the width of the absorbent core 42. Thus, the ear regions 60 and 62 are those portions that engage the side marginal portions of the wearer's waist and torso, whereas the central region 64 engages the medial portion of the wearer's waist and torso. The central region thus defines the transverse area of typical liquid deposition.

The air-laid fibrous webs of the present invention, such as the absorbent core 42 of FIG. 2, further comprise a dusting layer 76, having thickness $T_2$, and a continuous primary layer 74, having thickness $T_1$, with a core reinforcing layer 72 disposed between the dusting layer 76 and the primary layer 74. "Continuous", as used herein, means that the layer of the absorbent core which said term references is not interrupted by any additional reinforcing layers or analogous structural elements disposed within the interior of said layer, particularly structural elements which are substantially parallel to the core reinforcing layer between the primary and dusting layers. The dusting layer is preferably also continuous.

Figure 5:
FIG. 5 is a cross-sectional view of an absorbent core of the present invention.

FIG. 5 shows a cross sectional view of an absorbent core of the present invention, having primary layer 74, dusting layer 76, and core reinforcing layer 72 disposed between primary layer 74 and dusting layer 76. Also, shown are thicknesses $T_1$ and $T_2$ in more detail than can be seen in FIG. 2. Specifically, FIG. 5 shows that thicknesses of the fibrous absorbent core layers $T_1$ and $T_2$, are to be measured exclusive of the thickness of the core reinforcing layer 72. Other thickness measurements for fibrous absorbent core layers discussed herein similarly exclude any core reinforcing layers.

The preferred disposable absorbent diapers of the present invention are characterized by the absence of the core-enveloping reinforcing elements, or any other structural elements interposed between the absorbent core and the topsheet and/or between the absorbent core and the backsheet, previously utilized for high integrity cores made with primarily mechanical pulp fibers, sucn as described in U.S. Pat. No. 4,327,729, L. W. King, "Low-Density Disposable Absorbent Having Low Stretch, Wet Strength Center Ply to Provide Improved Pad Integrity," issued May 4, 1982, which includes enveloping tissue plies in addition to an internal core reinforcing layer in the context of low density absorbent cores. Additionally, the absorbent cores of the diapers of the present invention have sufficient structural integrity such that they needn't have, and preferably do not have, areas upon which portions of the core are folded or layered over itself, such that a vertical cross section of the absorbent core includes only a single occurrence of the dusting layer, a single occurrence of the primary layer, and a single occurrence of the core reinforcing layer. Surprisingly, the absorbent cores of the present invention exhibit good core integrity while being capable of providing excellent fluid absorption performance.

While the absorbent cores of the diapers of the present invention do not have an enveloping tissue layer and do not have portions of the core that are folded or layered over itself, in one contemplated embodiment of the invention a liquid pervious sheet is disposed between the topsheet and the absorbent core, without being connected or otherwise fixably associated with the topsheet or the absorbent core. Such a sheet which can be made from the same materials as the topsheet, or other material such as CTMP tissue, may be provided as a precautionary measure to further inhibit polymeric gelling material utilized in the absorbent core from contacting the wearer's skin.

The diapers of the present invention are generally characterized by an absorbent core of the above construction disposed between a topsheet and backsheet of a diaper, wherein the fibers utilized in the core are primarily mechanical pulp fibers. The primary layer and the dusting layer being continuous, there are no other sheets or other structural elements incorporated into these core element layers other than the core reinforcing layer which separates the primary and dusting layers. The preferred diapers are further characterized by having no other structural reinforcing elements disposed between the topsheet and backsheet, respectively, and the absorbent core. Thus, the essential structural elements of the preferred diaper can be characterized by the absorbent core, including the interior core reinforcing layer, the continuous primary layer, including the polymeric gelling material, the continuous dusting layer and the topsheet and backsheet (which are associated together as described above). Other features, structures, and elements directed toward other aspects of diaper performance such as, but not limited to, fit and leakage features, additional polymeric gelling material (such as in the dusting layer), etc., are not meant to be excluded from the scope of the invention.

The core reinforcing layer for use herein are liquid pervious, permitting liquids to readily penetrate through its thickness. They can be made from a wide range of materials, including those materials useful for topsheets, as described above. Substrate materials include porous foams, reticulated foams, apertured plastic films, tissue sheets from natural fibers (e.g., cellulosic fibers such as cotton or wood fibers, including mechanical pulp fibers such as CTMP), synthetic fibers (e.g., polyester or polypropylene fibers) or a combination of such natural and/or synthetic fibers. They can also be treated with material that enables the core reinforcing layer to maintain a significant portion of their strength subsequent to wetting. Such treatment, which would include wet strength resins such as are well known in the art, would be particularly suitable in the case of core reinforcing layers made from natural cellulosic fibers.

There are a number of manufacturing techniques which may be used to manufacture the core reinforcing layer, including those techniques that can be used to manufacture topsheets, as described above. For example, the core reinforcing layer may be woven, nonwoven, spunbonded, carded, or the like. Preferably, the core reinforcing layer has a weight from about 15 to about 25 grams per square meter, a minimum dry tensile strength of at least about 400 grams per centimeter preferably at least about 800 grams per centimeter in the machine direction and a wet tensile strength of at least about 55 grams per centimeter in the cross machine direction. Tensile strength is measured, for purposes herein, according to Tappi Method T-404 utilizing a Model TM Instron tensile tester, as manufactured by Instron Engineering Corporation of Canton, Mass., USA.

A preferred core reinforcing layer comprises staple length polypropylene fibers having a denier of about 1.5, such as Hercules type 151 polypropylene marketed by Hercules, Inc. of Wilmington, Del. This material is generally made by carding and thermal bonding. An especially preferred material for the core reinforcing layer is spunbonded polypropylene such as LUTRASOL (available from Lutrevil Spinvlies, Federal Republic of Germany) having a basis weight of about 19 $g/m^2$. Other commercial materials include: HOLMESTRA (spunbonded polypropylene nonwoven material available from HJR Fiberweb, Norrkoping, Sweden); PRO-FLEECE (dry laid, thermally bonded polypropylene nonwoven material available from Amoco Fabrics, Niederlassung der Amoco Deutschland GmbH, Gronau, F.R.G.); and LUTRASIL (spunbonded polyamide available from Freudenberg Spunweb, Durham, N.C., U.S.A.).

The dusting layer 76 is comprised of mechanical pulp fibers. The primary layer 74 is comprised of mechanical pulp fibers and discrete particles of polymeric gelling agent.

As used herein, the term "mechanical pulp fibers" shall mean pulp fibers derived from wood which retain a substantial portion of the lining present in the unpulped wood. Preferably, greater than about 80% yield based upon the weight of the unpulped wood will be retained. The mechanical pulp fibers should have an average fiber length of at least about 1.9 mm, preferably at least about 2.1 mm, preferably, the mechanical pulp has a fines content of less than about 15%, as measured according to the Bauer McNett Screen Test, and a Canadian Standard Freeness (CSF) of at least 200 CSF, preferably at least about 580 CSF. Typically, the CSF will be less than about 700 for practical reasons, although higher CSF pulp can be used. Average fiber lengths in conjunction with the description are to be calculated according to Tappi Standard Method No. T233-05-75 based on data from a Clark Classifier.

One type of mechanical pulp fibers which can be used is known in the art as thermomechanical pulp (TMP). TMP pulp fibers are produced by steaming wood chips at elevated temperature and pressure to soften the lining in the wood chips. Steaming the wood softens the lining, thereby reducing the amount of mechanical energy needed for fiberization and consequently facilitating the production of longer, less damaged fibers and lower presence of fines than obtainable with more rudimentary mechanical pulp fibers, such as groundwood, which does not involve a steaming step. Suitable processes for making TMP are described by Asplund and his coworkers, as disclosed, for example, in U.S. Pat. No. 2,008,892 (July 23, 1935), incorporated by reference herein.

The highly preferred type of mechanical pulp fibers for use in conjunction with the present invention are chemithermomechanical pulp (CTMP) fibers, also sometimes referred to as chemically-modified thermomechanical pulp fibers. In CTMP processes, wood chips are given a mild chemical treatment in addition to a heating or steaming step prior to mechanical defiberization. The chemical treatment, generally a sulfonation or alkali treatment, is limited so as to merely soften the lignin rather than remove it as in conventional chemical pulping processes. This chemical treatment further decreases defiberization energy and allows longer defibrated fibers to be formed.

A variant of CTMP for which an analogous chemical treatment has been applied is known as chemimechanical pulp, which omits the steaming step practiced in the manufacture of TMP and CTMP. It is also known to chemically treat the pulp after the start or completion of mechanical defibration. Such treatment can be applied to pulp which has not been previously chemically treated, or to pulp which has been previously chemically treated.

Workers such as Beverage and Keough in U.S. Pat. No. 2,422,522 (June 17, 1947), Beverage, Keough and Surino in U.S. Pat. No. 2,425,024 (Aug. 5, 1947) and Asplund, Cederquist and Reinhall in U.S. Pat. No. 3,338,525 (Aug. 29, 1967), all incorporated by reference herein, have generally described mechanical pulping processes Ford and Gardner, in U.S. Pat. No. 4,116,758 (Sept. 26, 1978), incorporated by reference herein, have described a mechanical pulping process for producing highly sulfonated CTMP pulp which also can be of use for the present invention. The mechanical pulp of this invention will generally be derived primarily from softwood (gymnosperm) wood sources, although hardwood species can also be used. Any of the softwood species commonly used for making pulp can be used. Suitable species include, but are not limited to, Picea glauca (white spruce), Picea mariana (black spruce), Picea rubra (red spruce), Pinus strobus (white pine), Pinus caribeau (slash pine), and Pinus tadia (loblolly pine).

Commercial sources of CTMP pulp include: Cascades (Port Cartier) Inc. (Quebec, Canada) which markets CTMP pulp from its Port Cartier pulp mill; Stora Cell AB (Skoghall, Sweden); and Metsa-Serla Group (Tampere, Finland), which markets CTMP from its Lielahti CTMP mill.

The mechanical pulp fibers used in the fibrous webs should be in an individualized state referred to in the art as "fluff". The fluff should have a disintegration state of at least about 85%, preferably at least about 90%, more preferably at least about 95%. Higher disintegration states, up to the maximum of 100%, can be used so long as the previously described fiber length criteria are met. However, such high disintegration states may be limited in practice in high speed production lines for practical and processing reasons. The disintegration state, for purposes herein, shall be determined according to the Disintegration State Procedure provided below.

In addition to mechanical pulp fibers, the primary layer 74 also comprises discrete particles of substantially water-insoluble polymeric gelling material. Polymeric gelling agents are optionally present in the dusting layer 76, in addition to being essentially present in the primary layer of the absorbent cores.

Suitable polymeric gelling materials can be inorganic materials such as silica gels or organic compounds such as cross-linked polymers Cross-linking may be by covalent, ionic, vander Waals, or hydrogen bonding. Examples of polymeric gelling materials include polyacrylamides, polyvinyl alcohol, ethylene maleic anhydride copolymers, polyvinyl ethers, hydroxypropyl cellulose, carboxymethyl cellulose, polyvinyl morpholinone, polymers and copolymers of vinyl sulfonic acid, polyacrylates, polyacrylamides, polyvinyl pyridone and the like. Other suitable Preferred polymeric gelling materials are those disclosed in Assarason et U.S. Pat. No. 3,901,236, issued Aug. 26, 1975, the disclosure of which is incorporated herein by reference. polymeric gelling materials for use in the absorbent core are hydrolyzed acrylonitrile grafted starch, acrylic acid grafted starch, polyacrylates, and isobutylene maleic anhydride copolymers, or mixtures thereof. More preferred are the polyacrylates and the acrylic acid grafted starch polymeric gelling materials.

Processes for preparing polymeric gelling materials are in Masuda et al., U.S. Pat. No. 4,076,663, issued Feb. 28, 1978; in Tsubakimoto et al., U.S. Pat. No. 4,286,082, issued Aug. 25, 1981; and further in U.S. Pat. Nos. 3,734,876, 3,661,815, 3,670,731, 3,664,343, 3,783,871, and Belgian Patent No. 785,850, the disclosures of which are incorporated herein by reference.

Particularly preferred polymeric gelling materials are the polyacrylates described in U.S. Pat No. 32,649 issued to K. A. Brandt et al. on Apr. 19, 1988, which is incorporated herein by reference.

The preferred polymeric gelling materials, referred to as hydrogel forming material in U.S. Pat. No. 32,649, are characterized generally by consisting essentially of (a) from about 50 mole percent to 99.999 mole percent of polymerized unsaturated, polymerizable; and (b) from about 0.001 mole percent to 5 mole percent of a cross-linking agent; wherein the composition has a degree of neutralization of at least about 25% and is substantially free of graft polymerizable polymer moieties; and further wherein said polymer composition, upon neutralization to a degree of neutralization of at least 50%, has or would have a gel volume of at least about 20 grams of synthetic urine per gram of hydrogel-forming polymer, a gel strength such that the hydrogel formed from said polymer exhibits a shear modulus of at least about 3270 dynes/cm$^2$, an initial extractable polymer content, after one hour in synthetic urine, of no more than about 7.5% by weight of hydrogel-forming polymer, and an equilibrium extractable polymer content, at equilibrium in synthetic urine, of no more than about 17% by weight of hydrogel-forming polymer, such descriptive limits being determined according to the techniques disclosed in U.S. Pat. No. 32,649.

The polymeric gelling agents used in the primary layer herein, and optionally in the dusting layer, are in the form of discrete particles. Polymeric gelling agents can be of any shape, e.g., spherical or semi-spherical, cubic, rod-like, polyhedral, etc. Shapes having a large greatest dimension/smallest dimension ratio, like needles, flakes and fibers, are also contemplated for use herein. Conglomerates of polymeric gelling agents particles may also be used.

Although the polymeric gelling agent webs herein are expected to perform well with particles having a particle size varying over a wide range, other considerations may preclude the use of very small or very large particles. For reasons of industrial hygiene, average particle sizes smaller than about 30 microns are less desirable. Particles having a smallest dimension larger than about 2 mm may also cause a feeling of grittiness in the absorbent article, which is undesirable from a consumer aesthetics standpoint. Furthermore, rate of fluid absorption can be affected by polymeric gelling agents particle size. Larger particles typically have very much reduced rates of absorption. Preferred for use herein are polymeric gelling agent particles having an average particle size of from about 50 microns to about 1 mm. "Particle Size" as used herein means the weighted average of the smallest dimension of the individual particles.

The relative amount of polymeric gelling agent fiber material and polymeric gelling agent particles used in the primary layer of the absorbent cores of the articles herein can be most conveniently expressed in terms of a weight percentage (dry weight basis) of the primary layer. The primary layer of the absorbent cores herein contain from about 8% to 60%, preferably from about 12% to 25%, more preferably from about 14% to about 18%, most preferably about 16%, by weight of the primary layer of polymeric gelling agents.

The density and basis weight of the polymeric gelling agent containing primary layer of the absorbent core can be of some importance in determining the absorbent properties of the resulting absorbent article. The average dry density of the primary layer should be in the range of from about 0.06 to about 0.30 g/cm$^3$, and more preferably within the range of from about 0.12 to about 0.18 g/cm$^3$. Typically the average dry basis weight of the primary layer is from about 0.01 to 0.20 g/cm$^2$, preferably from about 0.02 to about 0.12 g/cm$^2$. The same ranges of density can be utilized for the dusting layer, however average basis weight of the dusting layer preferably is between about 0.01 g/cm$^2$ and about 0.12 g/cm$^2$, preferably about 0.01 g/cm$^2$ to about 0.10 g/cm$^2$. Also preferably, the dusting layer will have a thickness (i.e., caliper) which is preferably from about ⅕ to about ⅗, preferably about 2/5 of the thickness of the primary layer. Also preferably, the absorbent core will have an average basis weight of between 0.04 g/cm$^2$ and about 0.15 g/cm$^2$. Typically, the primary layer and dusting layer will have approximately the same density for absorbent cores not having profiled density or basis weight, as discussed in more detail below. Density values for the primary and dusting layers are calculated from basis weight and layer caliper measured on newly unpacked, unfolded and dissected articles Caliper is measured according to Tappi Standard Method T-411. Density and basis weight values include the weight of the polymeric gelling agent particles.

In a preferred embodiment of the present invention, the primary layer will comprise an intimate admixture of mechanical pulp fiber material and polymeric gelling agent particles with the polymeric gelling agent particles being substantially uniformly distributed throughout a hydrophilic fiber matrix. Fibrous web layers of this type can be formed by air-laying a dry mixture of the fibers and polymeric gelling agent particles and densifying the resulting web. Such a procedure is described more fully in Procter & Gamble; European Patent Publication No. EP-A-No. 122,042; Published Oct. 17, 1984, incorporated herein by reference. As indicated in this reference, the webs formed by this procedure for use as the primary layer will preferably comprise substantially unbonded fibers and will preferably have a moisture content of 10% or less.

The particles of polymeric gelling agent may be dispersed in various weight ratios throughout different regions and thicknesses of the primary layer or may be homogeneously dispersed throughout the entire primary layer. For example, the mixture of mechanical pulp fibers and particles of polymeric gelling agents may be disposed only in the deposition region 54 of the absorbent core 42 and not in the back section 48 or the end region 52.

The airlaid webs hereof can be made by processes known in the art for making two layer webs having an interior reinforcing layer such as described by Kenneth B. Buell in U.S. Pat. No. 4,141,772, issued Feb. 27, 1979, incorporated herein by reference. A preferred process for making the airlaid webs is described generally by John J. Angstadt in U.S. Pat. No. 4,765,780, issued Aug. 23, 1988, incorporated herein by refence. U.S. Pat. No. 4,765,780 discloses a process and apparatus for forming airlaid fibrous webs having a multiplicity of components, such as a two layer absorbent core with one layer having polymeric gelling agent homogenously blended therein and the other layer being substantially free of polymeric gelling agent. These two layers are formed using a single drum, by feeding the fluff to two separate chutes, with the fluff directed toward one of the chutes having polymeric gelling material added thereto. The fluff from each of the chutes is sequentially deposited onto the drum to provide a two layer web. In order to make the airlaid webs of the present invention with a core reinforcing layer, such as a nonwoven polypropylene material, utilizing the apparatus of the general type described in U.S. Pat. No. 4,765,780, the core reinforcement layer can be deposited upon the first layer of fluff deposited on the drum through the use of feed rolls positioned between the two fluff chutes such that the core reinforcement layer is sequentially deposited between the deposition of the two fluff layers. Air baffles, should be used to shield the feed rolls and core reinforcement layer material from air turbulence created by rotation of the drum. This can be done by routing the core reinforcement layer from the feed rolls through the orifice of an additional, conventional chute, such that said core reinforcement layer is deposited at a position sequentially between the chutes depositing the two fluff layers at an intermediate position on the drum between where the primary layer and the dusting layer are deposited making the present absorbent cores, else the core reinforcing layer would interfere with subsequent deposition of fibrous material.

The absorbent cores of the present invention preferably have density and basis weight profile to provide additional fibrous material in the region of bodily fluid discharge, such that the regions of bodily fluid discharge are characterized by a higher degree of capillarity relative to the rest of the absorbent core.

As used herein, the "region of fluid discharge" of the airlaid web corresponds to the proximate area of discharges made by the wearer of the diaper. With respect to FIGS. 2 and 4, this refers to the regions common with both the central regions 64 and 464 and the front regions 54 and 454, respectively. The portion of the absorbent core having increased density and basis weight can, of course, extend beyond the region of fluid discharge and also needn't encompass all of such discharge region. However, the said portion should be coextensive with at least part, and preferably all, of the fluid discharge region of an absorbent core.

The region of the diaper with increased density and basis weight may vary for diaper designs depending upon whether the diaper is intended for use by primarily males, primarily females, or both.

Figure 3:
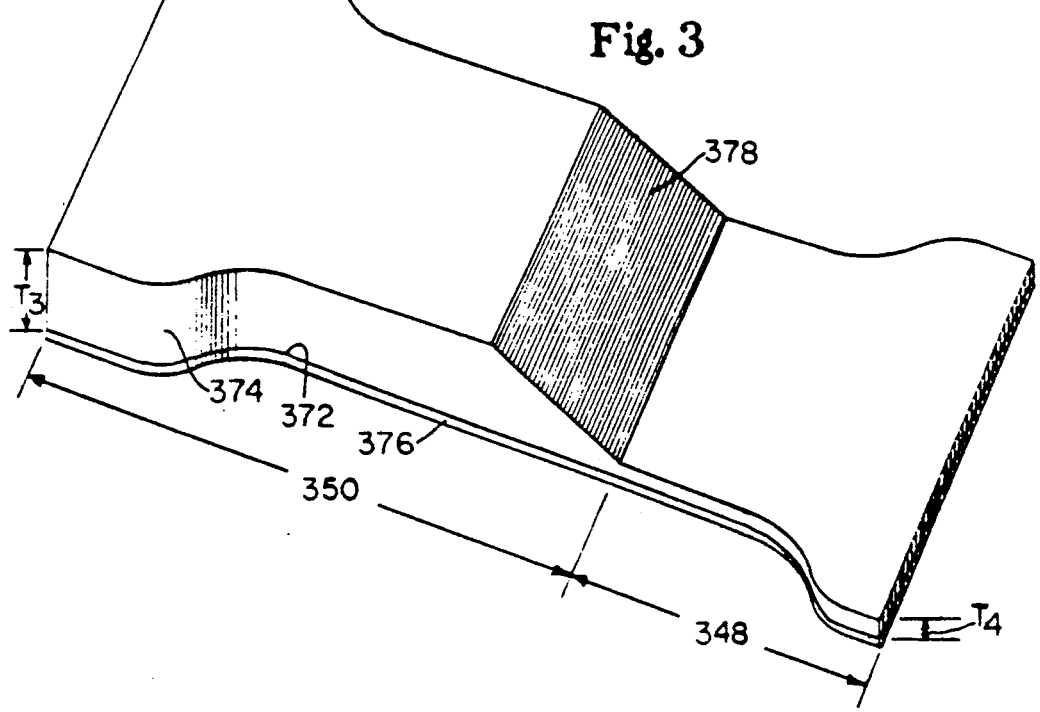
FIG. 3 is a perspective view of an alternate embodiment of an absorbent core that can be utilized in the present invention, wherein the absorbent core has a profiled basis weight and is shown prior to calendering.
Figure 4:
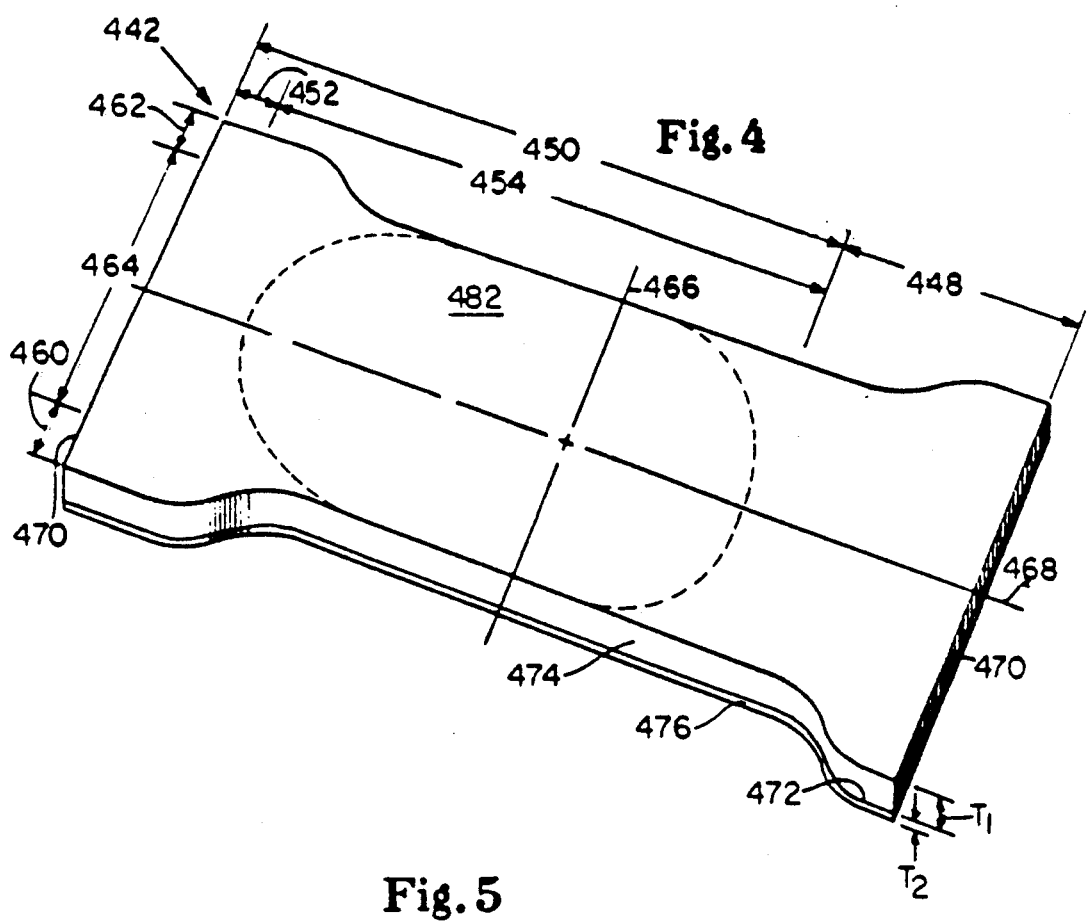
FIG. 4 is a perspective view of a further alternate embodiment of an absorbent core that can be utilized in the present invention, wherein the absorbent core has a profiled basis weight and density, and has been calendered to constant caliper.

FIGS. 3 and 4 show alternate embodiments of absorbent cores of the present invention that are especially designed for disposable diaper use whereby particularized regions of the absorbent cores have increased basis weight, alternately referred to herein as profiled basis weight.

FIG. 3 shows one alternative embodiment of an absorbent core 342 of the present invention which has a forward-profiled basis weight. The basis weight is profiled to provide a higher basis weight in the region of discharge by the user relative to the low based weight remainder of the absorbent core. Absorbent core 342 has primary 374, dusting layer 376, core reinforcing layer 372, a high basis weight front section 350, back section 348, and basis weight transition zone 378. As shown in FIG. 3, the front section 350 of the absorbent member 342 has a thickness T3, greater than the thickness T4, of the back section 348. The front section 350 of the absorbent core 342 has a terraced character by virtue of the thickness difference between the front section 350 and the back section 348 and by virtue of the relatively steep slope formed by a basis weight transition zone which is designated 378. Such a core can be made by airlaying a thickness profiled core-preform of substantially uniform density. Preferably, for uncalendered absorbent cores, T3 is at least about 1.5 times as great as T4 and preferably about 2.0 times as great as T4. Preferably, the absorbent core 342 is calendered, most preferably to approximately uniform caliper, to provide a front section 350 which is of about 1.5 times, preferably about 2.0 times, higher basis weight and density than the back section 348. The type of basis weight profile shown in FIG. 3 is particularly useful for diapers worn by male users. Preferred density and basis weight for the front section 350 are from about 0.12 $g/cm^3$ to about 0.30 $g/cm^3$, more preferably from about 0.12 $g/cm^3$ to about 0.18 $g/cm^3$, and from about 0.04 $g/cm^2$ to about 0.15 $g/cm^2$, most preferably from 0.08 $g/cm^2$ to 0.12 $g/cm^2$, respectively. The low basis weight remainder of the absorbent core preferably has an average basis weight of between about 0.01 $g/cm^2$ and about 0.06 $g/cm^2$; more preferably about 0.03 to about 0.05 $g/cm^2$.

FIG. 4 shows an embodiment of an absorbent core 442, having an alternate profiled basis weight, subsequent to calendering to uniform caliper. Absorbent core 442 has a back section 448, a front section 450 with an end region 452, a deposition region 454, ear regions 460 and 462, and central region 464, transverse centerline 466, longitudinal centerline 468, end edges 470, core reinforcing layer 472, primary layer 474, dusting layer 476, and a densified, high basis weight region 482. Absorbent core 442 has an elliptically-shaped densified region 482 which encompasses regions of typical discharge for male and female users. Such design is particularly useful for female users since the high basis weight region 482 is located, in use, primarily in proximity to the crotch of the wearer, where the discharges of female wearers are concentrated.

DISINTEGRATION STATE PROCEDURE

Three samples of dry disintegrated mechanical pulp fibers of approximately 0.75 g–1.25 g each are prepared by preconditioning state determination maintained at 23.0° C. ±1.0° C. and at 50% ±5% relative humidity for sufficient time for said fibers to equilibrate (8–12 hours of equilibration is typically sufficient). Each sample is weighed and any clumps of non-disintegrated fibers are removed. A clump, for purposes herein is any grouping of five or more fibers bonded together, typically by hydrogen bonding. A pair of hand-held tweezers are then used to hold and shake each clump, for the purpose of removing loose, non-bonded fibers. The clumps from each of the three samples of fibers are then weighed. The original masses of the three fiber samples are added together to determine the total fiber mass of the fiber samples. The masses of the clumps of nondisintegrated fibers are added together to determine the total nondisintegrated fiber mass. The Disintegration State is calculated as follows:

$$\text{Disintegration State}(\%) = \left[1.0 - \frac{\text{total nondisintegrated fiber mass}}{\text{total fiber mass of samples}}\right] \times 100 \qquad (I)$$

While particular embodiments of the present invention have been illustrated and described, it would be obvious to those skilled in the art that various changes and modifications can be made without departing from the spirit and scope of the invention. The invention is to be defined according to the following claims, which are intended to encompass such changes and modifications.

What is claimed is:

1. A disposable, absorbent diaper comprising:
   (a) a topsheet;
   (b) a liquid impervious backsheet associated with said topsheet; and
   (c) an absorbent core disposed between said topsheet and said backsheet, said absorbent core having:
      (i) a dusting layer of mechanical pulp fibers;
      (ii) a continuous primary layer of mechanical pulp fibers containing from about 8% to about 60%, on a total primary layer dry weight basis, of discrete particles of polymeric gelling material; and
      (iii) a water-permeable core reinforcing layer disposed between said dusting layer and said primary layer; wherein: said mechanical pulp fibers have an average fiber length of at least about 1.9 mm and are characterized by a Distintegration State of at least about 85%; said dusting layer has a basis weight of between about 0.01 g/cm² and about 0.20 g/cm² and density of between about 0.06 g/cm³ and about 0.30 g/cm³ and said primary layer has a basis weight of between about 0.01 g/cm² and about 0.20 g/cm² and a density of between about 0.06 g/cm³ and about 0.30 g/cm³ and said absorbent core is oriented such that said primary layer is disposed toward said topsheet and said dusting layer is disposed toward said backsheet.

2. A disposable absorbent diaper, as in claim 1, wherein said diaper is characterized by the absence of any structural elements interposed between said topsheet and said primary layer and between said backsheet and said dusting layer, and a vertical cross section of the absorbent core includes only one occurrence each of said dusting, primary, and core reinforcing layers.

3. A disposable absorbent diaper, as in claim 2, wherein the Disintegration State of the mechanical pulp fibers is at least about 90%.

4. A disposable, absorbent diaper, as in claim 3, wherein said mechanical pulp fibers are chemithermomechanical pulp fibers which have an average fiber length of at least about 2.1 mm.

5. A disposable, absorbent diaper, as in claim 4, wherein the Disintegration State is at least about 95%.

6. A disposable, absorbent diaper, as in claim 4, wherein said dusting layer is continuous.

7. A disposable, absorbent diaper, as in claim 6, wherein said primary layer contains from about 12% to about 25% of said polymeric gelling material.

8. A disposable, absorbent diaper, as in claim 7, wherein said primary layer contains from about 14% to about 18% of said polymeric gelling material.

9. A disposable, absorbent diaper, as in claim 8, wherein the primary layer has an average dry density of from about 0.12 g/cm³ to about 0.18 g/cm³ and an average dry basis weight of from about 0.02 g/cm² to about 0.12 g/cm², and said dusting layer has an average dry density of from about 0.12 g/cm³ to about 0.18 g/cm³ and an average dry basis weight of from about 0.01 g/cm² to about 0.10 g/cm², and wherein said absorbent core has an average basis weight of from about 0.04 g/cm² to about 0.15 g/cm².

10. A disposable, absorbent diaper, as in claim 9, wherein said absorbent core has a profiled basis weight with a high basis weight region having a said absorbent core having a basis weight of about 0.08 g/cm² to about 0.12 g/cm² and a low basis weight remainder of said absorbent core having a basis weight of from about 0.01 g/cm² to about 0.06 g/cm².

11. A disposable, absorbent diaper, as in claim 7, wherein the primary layer has an average dry density of from about 0.12 g/cm³ to about 0.18 g/cm³ and an average dry basis weight of from about 0.02 g/cm², and said dusting layer has an average dry density of from about 0.12 g/cm³ to about 0.18 g/cm³ and an average dry basis weight of from about 0.01 g/cm² to about 0.10 g/cm², and wherein said absorbent core has an average basis weight of from about 0.04 g/cm² to about 0.15 g/cm².

12. A disposable absorbent diaper, as in claim 11, wherein said absorbent core has a profiled basis weight with a high basis weight region having a said absorbent core having a basis weight of about 0.08 g/cm² to about 0.12 g/cm² and a low basis weight remainder of said absorbent core having a basis weight of from about 0.01 g/cm² to about 0.06 g/cm².

* * * * *

UNITED STATES PATENT AND TRADEMARK OFFICE
CERTIFICATE OF CORRECTION

PATENT NO. : 5,019,063
DATED : May 28, 1991
INVENTOR(S) : Mario S. Marsan and Leonard R. Thompson It is certified that error appears in the above-identified patent and that said Letters Patent is hereby corrected as shown below:

Column 7, line 66, after "Absorbent" the word --Bandage-- was left out.
Column 9, line 42, "lining" should be --lignin--
Column 9, line 60, "lining" should be --lignin--
Column 9, lines 61 and 62, "lining" should be --lignin--
Column 10, line 33, "processes" should be --processes.--
Column 11, line 12, "pyridone" should be --pyridine--.
Col. 11, line 13, "Preferred" should be deleted.
Column 11, line 24, "are in" should be --are disclosed in--
Column 11, line 35, "U.S. Pat." should be --Reissue Pat.--
Column 11, line 60, "any shape" should be --any desired shape--

Signed and Sealed this

Thirteenth Day of July, 1993

Attest:

MICHAEL K. KIRK

Attesting Officer

Acting Commissioner of Patents and Trademarks